United States Patent [19]

Gay

[11] 4,343,945
[45] Aug. 10, 1982

[54] 5-BENZAMIDO-3-TRICHLOROMETHYL-1,2,4-THIADIAZOLES AND THEIR USE AS HERBICIDES, FUNGICIDES AND INSECTICIDES

[75] Inventor: Walter A. Gay, Cheshire, Conn.

[73] Assignee: Olin Corporation, New Haven, Conn.

[21] Appl. No.: 292,451

[22] Filed: Aug. 13, 1981

Related U.S. Application Data

[63] Continuation-in-part of Ser. No. 6,302, Jan. 23, 1979.

[51] Int. Cl.³ .................... A01N 43/82; C07D 285/08
[52] U.S. Cl. .......................................... 548/128; 71/73; 71/90; 424/270; 260/544 D; 260/544 N
[58] Field of Search ........................................ 548/128

[56] References Cited

U.S. PATENT DOCUMENTS 3,770,749 11/1973 Phillips .............................. 548/128

4,163,048 7/1979 Ross et al. .......................... 548/128

*Primary Examiner*—Alton D. Rollins
*Attorney, Agent, or Firm*—William D. Sabo

[57] ABSTRACT

Disclosed are selected 5-benzamido-3-trichloromethyl-1,2,4-thiadiazole compounds of the formula:

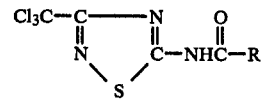

wherein R is phenyl which is unsubstituted or substituted by at least one member selected from the group consisting of lower alkyl having 1 to 4 carbon atoms, lower alkoxy having 1 to 4 carbon atoms, nitro and halo. These compounds are shown to have post-emergence herbicidal, fungicidal and insecticidal properties.

7 Claims, No Drawings

5-BENZAMIDO-3-TRICHLOROMETHYL-1,2,4-THIADIAZOLES AND THEIR USE AS HERBICIDES, FUNGICIDES AND INSECTICIDES

This application is a continuation-in-part of copending application Ser. No. 6,302, filed Jan. 23, 1979.

BACKGROUND OF THE INVENTION

1. Field of the Invention

This invention relates to selected 5-benzamido-3-trichloromethyl-1,2,4-thiadiazoles and their use as post-emergence herbicides, fungicides and insecticides.

2. Description of the Prior Art

Various 3,5-substituted 1,2,4-thiadiazole compounds have been known to possess different types of pesticidal activity such as fungicidal, herbicidal, insecticidal, nematocidal and the like. For example, U.S. Pat. No. 3,629,275, which issued to Carl Metzger et al. on Dec. 21, 1971, discloses the use of several 1,2,4-thiadiazol-5-yl amides as herbicides. These disclosed amide compounds differ from the present inventive compounds by having a 3-position substituent selected from an alkyl group having 1-4 carbon atoms or a phenyl group.

Furthermore, various 1,3,4-thiadiazole compounds have also been known to possess different types of pesticidal activity. For example, U.S. Pat. Nos. 3,728,354 and 4,092,148, which issued to Dietrich Rucker et al. and Tony Cebalo on Apr. 17, 1973 and May 30, 1978, disclose that certain amide derivatives of 1,3,4-thiadiazoles may be used as herbicides. However, it should be noted that 1,2,4-thiadiazoles and 1,3,4-thiadiazoles are treated as completely different classes of compounds by ordinarily skilled artisans in the pesticidal field because of their different modes of preparation, including the use of different starting materials.

BRIEF SUMMARY OF THE INVENTION

Accordingly, the present invention is directed to, as compositions of matter, selected 5-benzamido-3-trichloromethyl-1,2,4-thiadiazole compounds of the formula:

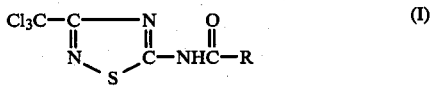

wherein R is phenyl which is unsubstituted or substituted by at least one member selected from the group consisting of lower alkyl having 1 to 4 carbon atoms, lower alkoxy having 1 to 4 carbon atoms, nitro and halo. The present invention also covers the use of these compounds as post-emergence herbicides, fungicides and insecticides.

DETAILED DESCRIPTION

The 5-benzamido compounds of the present invention may be prepared by reacting the corresponding 5-amino-3-trichloromethyl-1,2,4-thiadiazole with benzoyl chloride or the corresponding substituted benzoyl chloride. This general reaction is illustrated by the following Equation (A) wherein 5-amino-3-trichloromethyl-1,2,4-thiadiazole is reacted with benzoyl chloride.

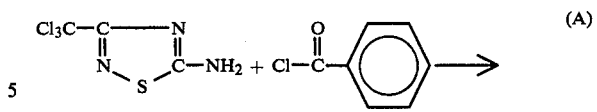

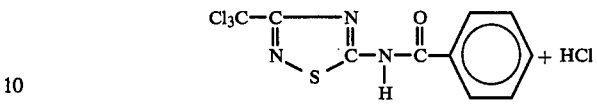

5-Amino-3-trichloromethyl-1,2,4-thiadiazole is described in U.S. Pat. No. 3,260,725, issued to H. A. Schroeder on July 12, 1966, and is made by reacting 5-chloro-3-trichloromethyl-1,2,4-thiadiazole with ammonia.

Benzoyl chloride may be made by reacting benzoic acid with thionyl chloride. The substituted benzoyl chloride reactants may generally be made by reacting the corresponding substituted benzoic acid with thionyl chloride. Benzoyl chloride and various substituted benzoyl chlorides are commercially available.

Illustrative substituted benzoyl chloride reactants for the compounds of the present invention include the following:

2-toluoyl chloride
3-toluoyl chloride
4-toluoyl chloride
4-anisoyl chloride
3-nitrobenzoyl chloride
4-nitrobenzoyl chloride
3,5-dinitrobenzoyl chloride
2-chlorobenzoyl chloride
2-fluorobenzoyl chloride
2,6-dichlorobenzoyl chloride
2,4-dichlorobenzoyl chloride.

Any conventional reaction conditions may be employed in the synthesis of the present compounds and the present invention is not intended to be limited to any particular reaction conditions. Advantageously and preferably, the reaction is carried out with an excess of the unsubstituted or substituted benzoyl chloride (e.g., from about 0.05 to about 20 moles excess) and in the presence of a suitable inert solvent. Xylene is a preferred solvent, but other inert solvents may be used. The reaction temperature and time will both depend upon many factors including the specific reactants being used. In most situations, reaction temperatures from about 0° C. to about 150° C. and reaction times from about 1 hour to about 30 hours may be preferred. The product may be recovered from the reaction mixture by any conventional means, for example, distillation, extraction or simply by cooling the reaction mixture and removing the precipitated product by filtration. Finally, it should be noted that while the reaction illustrated by Equation (A) is a preferred method of preparing compounds of the present invention, other synthesis methods may also be employed.

In accordance with the present invention, it has been found that compounds of Formula (I), above, may be used for defoliation or for desiccation of the green parts of plants. They are, in particular, suitable singly, or in mixtures thereof, for the control of weeds. As contemplated herein, the term "weeds" is meant to include not only weeds in the narrow sense, but also in the broad sense, whereby to cover all plants and vegetation considered undesirable for the particular purposes in question. Whether the active compounds according to the present invention act as total or selective herbicides depends essentially on the amount applied, as the artisan will appreciate.

Specifically, in practicing the process of the present invention, undesirable plant and vegetation are contacted with a herbicidally effective amount of the above-mentioned compounds. It is to be understood that the term "herbicidally effective amount" as used in the specification and claims herein is intended to include any amount that will kill or control said undesirable plants and vegetation when either employed by itself (i.e., in full concentration) or in sufficient concentration with a carrier or other substance. Of course, this amount may be constantly changing because of the possible variations in many parameters. Some of these may include: the number and type of plants to be controlled or killed; the type of loci or media to which the present compounds can be applied (e.g., weeds within crop areas, fence lines); degree of effectiveness required; and type of carrier, if any. The step of contacting may be accomplished by applying the present active compounds to the undesirable plants themselves or to the immediate locus or ground surrounding said plants. In most situations, the application of the compounds of the present invention in amounts from about 0.1 pound per acre to about 10 pounds per acre will be sufficient for selective or total herbicidal effect.

Furthermore, it has also been found that compounds of Formula (I), above, may be utilized as fungicides and insecticides. When the compounds are used as fungicides or insecticides, fungi or insects are contacted with a fungicidally or insecticidally effective amount of these compounds. It is to be understood that the terms "fungicidally effective amount" and "insecticidally effective amount" as used in the specification and claims herein are intended to include any amount that will kill or control said fungi or insects when either employed by itself (i.e., in full concentration) or in sufficient concentration within a carrier or other substance. Of course, this amount may be constantly changing because of the possible variations in many parameters. Some of these may include: the number and type of fungi or insects to be controlled or killed; the type of media to which the present compounds can be applied (e.g., plants or crops, insect breeding grounds); degree of effectiveness required; and type of carrier, if any.

This step of contacting may be accomplished by applying these compounds to the fungi or insects themselves, their habitat, breeding grounds, dietary media such as vegetation, crops and the like, and plant and animal life, including many which these pests may attack. In the case of fungi, it is preferable to apply the chemicals of the present invention to the dietary media or soil which they infest. In the case of insects, it may be advantageous to apply the chemicals of the present invention to the eggs of these insects, to the insects themselves, or to the insect larvae, the larvae habitat or the larvae dietary media. At the egg and larvae stages of the insect cycle, the insect is usually relatively stationary and the insecticide can be applied in a more economical fashion with a greater expectation of good results.

When the above-mentioned compounds of the present invention are used as herbicides, fungicides or insecticides, the compounds may be formulated and applied by any conventional methods that include using the compounds alone or with a carrier or other substances which may enhance the effectiveness of the chemical or facilitate handling. Moreover, the activity of the present compounds may be broadened by the addition thereto of other known biocides.

Specific methods of formulating and applying these active compounds include applying them in the form of dusts, dust or emulsion concentrates, wettable powders and concentrates, granulates, dispersions, sprays, solutions and the like.

The dusts and dust concentrate are usually prepared by simply grinding together the active compounds of the present invention with a finely divided inert diluent such as walnut flour, diatomaceous earth, fullers earth, attaclay, talc or kaolin. Dusts generally contain from about 1% to about 15% by weight of active compound and dust concentrates usually contain from about 16% to about 75% by weight of active compound. In practice, dust concentrates are usually admixed with more inert diluent at the site of use to form dusts before being applied to undesirable plant foliage or to plant foliage or animals which are to be protected from fungi or insect attack.

Wettable powders are generally prepared in the same manner as dust concentrates, but usually about 1% to about 10% by weight of a dispersing agent, for example, an alkali metal lignosulfonate and about 1% to about 10% of a surfactant, such as a nonionic surfactant, are incorporated in the formulation. For most applications, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray application.

It is possible to formulate granulates whereby these active compounds are dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, one of the above-mentioned active compounds, or more than one active compound, is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that such herbicide, fungicide or insecticide formulations, the ingredients which may make up such formulations other than the active compounds and the dosages, and means of applying these formulations may include all known and conventional substances, amounts and means, respectively, that are suitable for obtaining the desired herbicidal, fungicidal and/or insecticidal result. And, therefore, such process parameters are not critical to the present invention.

Fungicides and insecticides of the present invention may be effective for the control of broad classes of fungi and insects and the latter's eggs and larvae. Specific illustrations of fungi wherein fungicidal activity has been shown include bean rust, cucumber anthracnose, bean powdery mildew, rice leaf spot and potato late blight. A specific illustration of insects wherein insecticidal activity has been shown is Mexican bean beetle larvae.

The following examples further illustrate the present invention. All parts and percentages employed therein are by weight unless otherwise indicated.

EXAMPLE I

5-Benzamido-3-Trichloromethyl-1,2,4-Thiadiazole

A solution of 11.0 g (0.05 mole) 5-amino-3-trichloromethyl-1,2,4-thiadiazole and 14.1 g (0.1 mole) benzoyl chloride in 200 ml xylene was heated at reflux for 20 hours. Upon cooling to −10° C., 13.7 g (85% yield) of pure product precipitated from the reaction mixture and was isolated by filtration; m.p. 190° C.

| Analysis for $C_{10}H_6Cl_3N_3OS$: | | | | |
|---|---|---|---|---|
| | C | H | Cl | N |
| Calculated: | 37.23% | 1.88% | 32.97% | 13.03% |
| Found: | 37.42% | 2.09% | 32.72% | 12.89% |

EXAMPLE II 5-(2-Toluamido)-3-Trichloromethyl-1,2,4-Thiadiazole

A solution of 22.0 g (0.1 mole) 5-amino-3-trichloromethyl-1,2,4-thiadiazole and 16.0 g (0.1 mole) 2-toluoyl chloride in 250 ml xylene was heated at reflux for 20 hours. The reaction mixture was cooled to room temperature and the resulting precipitate removed by filtration. Following recrystallization for toluene, 11.8 g (35% yield) of pure product was otained; m.p. 170° C.

| Analysis for $C_{11}H_8Cl_3N_3OS$: | | | | |
|---|---|---|---|---|
| | C | H | N | Cl |
| Calculated: | 39.25% | 2.40% | 12.48% | 31.60% |
| Found: | 38.90% | 2.50% | 12.32% | 31.94% |

EXAMPLE III 5-(3-Toluamido)-3-Trichloromethyl-1,2,4-Thiadiazole

A solution of 22.0 g (0.1 mole) 5-amino-3-trichloromethyl-1,2,4-thiadiazole and 16.0 g (0.1 mole) 3-toluoyl chloride in 250 ml xylene was heated at reflux for 20 hours. The reaction mixture was cooled to room temperature and the resulting precipitate removed by filtration. The crude product was washed with petroleum ether and then recrystallized twice from toluene to obtain 4.0 g (12% yield) of pure product; m.p. 142° C.

| Analysis for $C_{11}H_8Cl_3N_3OS$: | | | | |
|---|---|---|---|---|
| | C | H | N | Cl |
| Calculated: | 39.25% | 2.40% | 12.48% | 31.60% |
| Found: | 38.95% | 2.78% | 12.29% | 31.44% |

EXAMPLE IV 5-(4-Toluamido)-3-Trichloromethyl-1,2,4-Thiadiazole

A solution of 11.0 g (0.05 mole) 5-amino-3-trichloromethyl-1,2,4-thiadiazole and 8.0 g (0.05 mole) 4-toluoyl chloride in 250 ml toluene was heated at reflux for 20 hours. Unreacted amino compound was removed by cooling the reaction mixture and filtering the precipitate. Concentration of the filtrate in vacuo gave the crude product, which was purified by recrystallization from cyclohexane. Yield was 9.1 g (27%); m.p. 127° C.

| Analysis for $C_{11}H_8Cl_3N_3OS$: | | | | |
|---|---|---|---|---|
| | C | H | N | Cl |
| Calculated: | 39.25% | 2.40% | 12.48% | 31.60% |
| Found: | 39.28% | 2.44% | 12.51% | 31.44% |

EXAMPLE V 5-(4-Anisamido)-3-Trichloromethyl-1,2,4-Thiadiazole

A solution of 11.0 g (0.05 mole) 5-amino-3-trichloromethyl-1,2,4-thiadiazole and 12.8 g (0.08 mole) 4-anisoyl chloride in 200 ml xylene was heated at reflux for 20 hours. Cooling of the reaction mixture resulted in precipitation of the crude product, which was then isolated by filtration. Purification was achieved by washing the crude product with hot hexane. Yield was 12.0 g (82%); m.p. 172° C.

| Analysis for $C_{11}H_8Cl_3N_3O_2S$ | | | | |
|---|---|---|---|---|
| | C | H | N | Cl |
| Calculated: | 37.47% | 2.29% | 11.92% | 30.16% |
| Found: | 37.58% | 2.33% | 11.91% | 29.93% |

EXAMPLE VI 5-(3-Nitrobenzamido)-3-Trichloromethyl-1,2,4-Thiadiazole

A solution of 21.8 g (0.1 mole) 5-amino-3-trichloromethyl-1,2,4-thiadiazole and 18.6 g (0.1 mole) 3-nitrobenzoyl chloride in 250 ml xylene was heated at reflux for 20 hours. Unreacted starting amino compound was recovered by cooling the reaction mixture and filtering the resulting precipitate. The filtrate was concentrated in vacuo and the residue recrystallized from xylene. After washing with petroleum ether, 25.4 g (69% yield) of pure product was obtained; m.p. 198° C.

| Analysis for $C_{10}H_5Cl_3N_4O_3S$: | | | | |
|---|---|---|---|---|
| | C | H | N | Cl |
| Calculated: | 32.67% | 1.37% | 15.24% | 28.93% |
| Found: | 32.91% | 1.40% | 15.16% | 28.51% |

EXAMPLE VII 5-(4-Nitrobenzamido)-3-Trichloromethyl-1,2,4-Thiadiazole

A solution of 10.9 g (0.05 mole) 5-amino-3-trichloromethyl-1,2,4-thiadiazole and 10.2 g (0.055 mole) 4-nitrobenzoyl chloride in 200 ml toluene was heated at reflux for 20 hours. Upon cooling to room temperature, the crude product precipitated from the reaction mixture and was isolated by filtration. After washing with hexane, 13.5 g (73% yield) of pure product was obtained; m.p. 214° C.

| Analysis for $C_{10}H_5Cl_3N_4O_3S$: | | | |
|---|---|---|---|
| | C | H | N | Cl |
| Calculated: | 32.67% | 1.37% | 15.24% | 28.93% |
| Found: | 32.61% | 1.39% | 15.30% | 29.04% |

EXAMPLE VIII

5-(3,5-Dinitrobenzamido)-3-Trichloromethyl-1,2,4-Thiadiazole

A solution of 10.9 g (0.05 mole) 5-amino-3-trichloromethyl-1,2,4-thiadiazole and 12.6 g (0.055 mole) 3,5-dinitrobenzoyl chloride in 200 ml toluene was refluxed for 20 hours. The crude product precipitated from the reaction mixture upon cooling to −10° C. After isolation by filtration, the residue was washed with hot petroleum ether and finally recrystallized from methylene chloride to give 17.5 g (85% yield) of pure product; m.p. 197° C.

| Analysis for $C_{10}H_4Cl_3N_5O_5S$: | | | |
|---|---|---|---|
| | C | H | N | Cl |
| Calculated: | 29.11% | 0.98% | 16.98% | 25.78% |
| Found: | 29.52% | 1.17% | 16.53% | 24.87% |

EXAMPLE IX

5-(2-Chlorobenzamido)-3-Trichloromethyl-1,2,4-Thiadiazole

A solution of 10.9 g (0.05 mole) 5-amino-3-trichloromethyl-1,2,4-thiadiazole and 17.5 g (0.10 mole) 2-chlorobenzoyl chloride was heated at reflux for 18 hours in 200 ml xylene. After concentration in vacuo, the resulting oil was triturated with cold hexane to give 14.9 g (85% yield) of crude product. Recrystallization from benzene/hexane gave a pure product; m.p. 142° C.

| Analysis for $C_{10}H_5Cl_4N_3OS$: | | | |
|---|---|---|---|
| | C | H | N | Cl |
| Calculated: | 33.64% | 1.41% | 11.77% | 39.72% |
| Found: | 33.90% | 1.54% | 11.82% | 39.50% |

EXAMPLE X

5-(2-Fluorobenzamido)-3-Trichloromethyl-1,2,4-Thiadiazole

A solution of 22.0 g (0.1 mole) 5-amino-3-trichloromethyl-1,2,4-thiadiazole and 16.0 g (0.1 mole) 2-fluorobenzoyl chloride in 250 ml xylene was heated at reflux for 20 hours. After filtration of the reaction mixture, the filtrate was concentrated to 30 ml whereupon a precipitation resulted. The precipitate was removed by filtration and recrystallized from benzene to give 3.4 g (10% yield) of pure product; m.p. 149° C.

| Analysis for $C_{10}H_5Cl_3FN_3OS$: | | | |
|---|---|---|---|
| | C | H | N | Cl |
| Calculated: | 35.25% | 1.48% | 12.34% | 31.24% |
| Found: | 35.31% | 1.60% | 12.11% | 31.19% |

EXAMPLE XI

5-(2,6-Dichlorobenzamido)-3-Trichloromethyl-1,2,4-Thiadiazole

A solution of 22.0 g (0.1 mole) 5-amino-3-trichloromethyl-1,2,4-thiadiazole and 20.1 g (0.1 mole) 2,6-dichlorobenzoyl chloride was refluxed for 8 hours in 200 ml dichlorobenzene. After filtration, the crude product precipitated from the filtrate upon standing. Recrystallization from toluene gave 8.6 g (22% yield) of pure product; m.p. 209° C.

| Analysis for $C_{10}H_4Cl_5N_3OS$: | | | |
|---|---|---|---|
| | C | H | N | Cl |
| Calculated: | 30.68% | 1.03% | 10.73% | 45.28% |
| Found: | 30.60% | 1.10% | 10.72% | 45.09% |

EXAMPLE XII

5-(2,4-Dichlorobenzamido)-3-Trichloromethyl-1,2,4-Thiadiazole

A solution of 10.9 g (0.05 mole) 5-amino-3-trichloromethyl-1,2,4-thiadiazole and 20.9 g (0.10 mole) 2,4-dichlorobenzoyl chloride was refluxed in 200 ml xylene for 20 hours. The reaction mixture was concentrated in vacuo and the resulting residue extracted with benzene. Addition of hexane resulted in precipitation of 13.6 g (69% yield) pure product; m.p. 136° C.

| Analysis for $C_{10}H_4Cl_5N_3OS$: | | | |
|---|---|---|---|
| | C | H | N | Cl |
| Calculated: | 30.68% | 1.03% | 10.74% | 45.28% |
| Found: | 30.83% | 1.11% | 10.95% | 45.00% |

HERBICIDE SCREEN

The active materials made in the preceding examples were tested for activity as effective herbicides by the following method.

A uniform aqueous dispersion of each chemical was made by dissolving the chemical in a solution of acetone containing a nonionic surfactant in a concentration of 500 ppm. The resulting solution was diluted with water (1:9) to obtain a mixture of 10% acetone, 50 ppm surfactant, 0.208% by weight test candidate as shown in the following Table I, and the balance water; 50 milliliters of this solution applied to a flat of 144 square inches corresponds to 10 lb/acre.

The aqueous solutions containing each chemical were applied to flats seeded with representative monocotyledonous and dicotyledonous plants. The test chemical was applied to a flat after the first true plant leaves had developed (post-emergence screening). Response was rated 12 to 21 days after treatment on a scale of 0 to 10, where 0 represents no injury and 10 represents complete kill.

The crops and weeds used for the determination of activity were Foxtail Millet (*Setaria italica*), Japanese Millet (*Echinochloa crusgalli*), Crabgrass (*Digitaria sanguinalis*), Wild Oats (*Avena fatua*), Morning Glory (*Ipomoea purpurea*), Mustard (*Brassica nigra*), Pigweed (*Amaranthus retroflexus*), Sesbania (*Sesbania exaltata*), Velvet Leaf (*Abutilon theophrasti*), Soybean (*Glycine max*), Cotton (*Gossypium hirsutum*), Tomato (*Lycopersicon esculentum*) and Cocklebur (*Xanthium spp.*).

The following Table I illustrates the herbicidal activity claimed for the compounds of this invention. Table I shows the results of general testing at 10 lb/acre in the post-emergence screen.

obtain a stock solution of 10% by volume acetone and 90% by volume water with 50 ppm TRITON X-155 and the test chemical contained therein.

[1] Manufactured by Rohm and Haas of Philadelphia, Pennsylvania and is a polyether alcohol.

TABLE I

HERBICIDE* ACTIVITY AT 10 LB/ACRE

| Test Chemical | CROPS | | | GRASSES | | | |
|---|---|---|---|---|---|---|---|
| | SOYBEAN | COTTON | TOMATO | FOXTAIL MILLET | JAPANESE MILLET | CRABGRASS | WILD OATS |
| 5-Benzamido-3-Trichloromethyl-1,2,4-Thiadiazole | 3 | 3 | 10 | 5 | 0 | 2 | 5 |
| 5-(2-Toluamido)-3-Trichloromethyl-1,2,4-Thiadiazole | 0 | — | 0 | 2 | 3 | 4 | 0 |
| 5-(3-Toluamido)-3-Trichloromethyl-1,2,4-Thiadiazole | 0 | 0 | 0 | 0 | 0 | 0 | 0 |
| 5-(4-Toluamido)-3-Trichloromethyl-1,2,4-Thiadiazole | 0 | 0 | 0 | 0 | 0 | 0 | 0 |
| 5-(4-Anisamido)-3-Trichloromethyl-1,2,4-Thiadiazole | 3 | 1 | 1 | 1 | 1 | 1 | 2 |
| 5-(3-Nitrobenzamido)-3-Trichloromethyl-1,2,4-Thiadiazole | 2 | — | 5 | 0 | 2 | 0 | 0 |

| Test Chemical | BROAD-LEAF WEEDS | | | | | |
|---|---|---|---|---|---|---|
| | MORNING GLORY | MUSTARD | PIGWEED | SESBANIA | VELVET LEAF | COCKLEBUR |
| 5-Benzamido-3-Trichloromethyl-1,2,4-Thiadiazole | 7 | 10 | 9 | 5 | 10 | — |
| 5-(2-Toluamido)-3-Trichloromethyl-1,2,4-Thiadiazole | 2 | 2 | 2 | 0 | 0 | 0 |
| 5-(3-Toluamido)-3-Trichloromethyl-1,2,4-Thiadiazole | 0 | 0 | 0 | 0 | 0 | 0 |
| 5-(4-Toluamido)-3-Trichloromethyl-1,2,4-Thiadiazole | 0 | 0 | 0 | 0 | 0 | 0 |
| 5-(4-Anisamido)-3-Trichloromethyl-1,2,4-Thiadiazole | 0 | 2 | 5 | 0 | 0 | — |
| 5-(3-Nitrobenzamido)-3-Trichloromethyl-1,2,4-Thiadiazole | 2 | 0 | 8 | 0 | 0 | 2 |

| Test Chemical | CROPS | | | GRASSES | | | |
|---|---|---|---|---|---|---|---|
| | SOYBEAN | COTTON | TOMATO | FOXTAIL MILLET | JAPANESE MILLET | CRABGRASS | WILD OATS |
| 5-(4-Nitrobenzamido)-3-Trichloromethyl-1,2,4-Thiadiazole | 0 | 0 | 4 | 0 | 0 | 0 | 0 |
| 5-(3,5-Dinitrobenzamido)-3-Trichloromethyl-1,2,4-Thiadiazole | 0 | 2 | 0 | 0 | 0 | 0 | 0 |
| 5-(2-Chlorobenzamido)-3-Trichloromethyl-1,2,4-Thiadiazole | 2 | 0 | 0 | 4 | 4 | 2 | 0 |
| 5-(2-Fluorobenzamido)-3-Trichloromethyl-1,2,4-Thiadiazole | 2 | — | 10 | 0 | 2 | 3 | 3 |
| 5-(2,6-Dichlorobenzamido)-3-Trichloromethyl-1,2,4-Thiadiazole | 2 | — | 3 | 3 | 3 | 0 | 0 |
| 5-(2,4-Dichlorobenzamido)-3-Trichloromethyl-1,2,4-Thiadiazole | 5 | 0 | 6 | 0 | 0 | 0 | 0 |

| Test Chemical | BROAD-LEAF WEEDS | | | | | |
|---|---|---|---|---|---|---|
| | MORNING GLORY | MUSTARD | PIGWEED | SESBANIA | VELVET LEAF | COCKLEBUR |
| 5-(4-Nitrobenzamido)-3-Trichloromethyl-1,2,4-Thiadiazole | 0 | 5 | 10 | 0 | 0 | — |
| 5-(3,5-Dinitrobenzamido)-3-Trichloromethyl-1,2,4-Thiadiazole | 5 | 0 | 3 | 0 | 0 | — |
| 5-(2-Chlorobenzamido)-3-Trichloromethyl-1,2,4-Thiadiazole | 3 | 7 | 3 | 0 | 0 | — |
| 5-(2-Fluorobenzamido)-3-Trichloromethyl-1,2,4-Thiadiazole | 5 | 7 | 3 | 6 | 9 | 9 |
| 5-(2,6-Dichlorobenzamido)-3-Trichloromethyl-1,2,4-Thiadiazole | 5 | 4 | 0 | 0 | 0 | 0 |
| 5-(2,4-Dichlorobenzamido)-3-Trichloromethyl-1,2,4-Thiadiazole | 6 | 8 | 9 | 3 | 4 | — |

*Post-emergence

The active materials formed in the examples were then tested for activity as effective foliar fungicides and as effective insecticides.

A uniform aqueous dispersion of each chemical was first prepared. These dispersions were made by dissolving each chemical in a solution of acetone containing the surfactant TRITON X-155[1] (concentration 500 ppm). Next, this solution was diluted with water (1:9) to The aqueous solutions containing each chemical were applied to various plants according to the methods stated below. These tests were designed to evaluate the ability of the chemical to protect non-infected foliage and eradicate recently established infection against major types of fungi such as rust, anthracnose, mildew, leaf spot and blight that attack above-ground parts of plants.

BEAN RUST

In primary screening, Pinto beans, which were in 2½ inch pots and 9 to 12 days old, were sprayed while rotating the plants on a turntable with an aqueous solution of each chemical of the examples. The aqueous solutions contained 260 ppm of each active chemical. Simultaneously, the soil in each pot was drenched with aqueous solutions of each chemical in the amount of 25 lb/acre. After the spray deposit had dried, the plants were atomized with a suspension of uredospores [summer spore stage of bean rust (*Uromyces phaseoli*)] and placed in a moist chamber at 70° F. for 24 hours. After 7 days, the severity of pustule formation was rated on a scale of from 0 (no inhibition) to 10 (complete inhibition). The test results are given in Table II below.

TABLE II

| FUNGICIDAL ACTIVITY AGAINST BEAN RUST | |
|---|---|
| Test Chemical | Primary Screening 25 lb/acre drench and 260 ppm spray |
| 5-Benzamido-3-Trichloromethyl-1,2,4-Thiadiazole | 10 |
| 5-(2-Toluamido)-3-Trichloromethyl-1,2,4-Thiadiazole | 10 |
| 5-(3-Toluamido)-3-Trichloromethyl-1,2,4-Thiadiazole | 9 |
| 5-(4-Toluamido)-3-Trichloromethyl-1,2,4-Thiadiazole | 8 |
| 5-(4-Anisamido)-3-Trichloromethyl-1,2,4-Thiadiazole | 5 |
| 5-(3-Nitrobenzamido)-3-Trichloromethyl-1,2,4-Thiadiazole | 6 |
| 5-(4-Nitrobenzamido)-3-Trichloromethyl-1,2,4-Thiadiazole | 10 |
| 5-(3,5-Dinitrobenzamido)-3-Trichloromethyl-1,2,4-Thiadiazole | 8 |
| 5-(2-Chlorobenzamido)-3-Trichloromethyl-1,2,4-Thiadiazole | 10 |
| 5-(2-Fluorobenzamido)-3-Trichloromethyl-1,2,4-Thiadiazole | 10 |
| 5-(2,6-Dichlorobenzamido)-3-Trichloromethyl-1,2,4-Thiadiazole | 8 |
| 5-(2,4-Dichlorobenzamido)-3-Trichloromethyl-1,2,4-Thiadiazole | 10 |

CUCUMBER ANTHRACNOSE

For the primary screening, two-week old cucumber plants were atomized with a suspension of cucumber anthracnose spores (*Collectrotrichium lagenarium*) and placed in a moist chamber at 70° F. for 24 hours. In the primary screening, the young plants were then sprayed while rotating the plants on a turntable with an aqueous solution that contained 260 ppm by weight of the active chemicals of Examples 1-12. Simultaneously, the soil in each pot was drenched with aqueous dispersions of each chemical in the amount of 25 lb/acre. After 5 days, the severity of pustule formation was rated on a scale of 0 (no inhibition) to 10 (complete inhibition). See Table III for the results of these tests.

TABLE III

| FUNGICIDAL ACTIVITY AGAINST CUCUMBER ANTHRACNOSE | |
|---|---|
| Test Chemical | Primary Screening 25 lb/acre drench and 260 ppm spray |
| 5-Benzamido-3-Trichloromethyl-1,2,4-Thiadiazole | 8 |

TABLE III-continued

| FUNGICIDAL ACTIVITY AGAINST CUCUMBER ANTHRACNOSE | |
|---|---|
| Test Chemical | Primary Screening 25 lb/acre drench and 260 ppm spray |
| 5-(2-Toluamido)-3-Trichloromethyl-1,2,4-Thiadiazole | 9 |
| 5-(3-Toluamido)-3-Trichloromethyl-1,2,4-Thiadiazole | 8 |
| 5-(4-Toluamido)-3-Trichloromethyl-1,2,4-Thiadiazole | 3 |
| 5-(4-Anisamido)-3-Trichloromethyl-1,2,4-Thiadiazole | 0 |
| 5-(3-Nitrobenzamido)-3-Trichloromethyl-1,2,4-Thiadiazole | — |
| 5-(4-Nitrobenzamido)-3-Trichloromethyl-1,2,4-Thiadiazole | — |
| 5-(3,5-Dinitrobenzamido)-3-Trichloromethyl-1,2,4-Thiadiazole | 5 |
| 5-(2-Chlorobenzamido)-3-Trichloromethyl-1,2,4-Thiadiazole | 9 |
| 5-(2-Fluorobenzamido)-3-Trichloromethyl-1,2,4-Thiadiazole | 8 |
| 5-(2,6-Dichlorobenzamido)-3-Trichloromethyl-1,2,4-Thiadiazole | 2 |
| 5-(2,4-Dichlorobenzamido)-3-Trichloromethyl-1,2,4-Thiadiazole | — |

BEAN POWDERY MILDEW

Bean plants with incipient infection of bean powdery mildew (*Erysiphe polygoni* DC) in 2½ inch pots were atomized (sprayed) with an aqueous solution of the chemicals of Examples 1-12. The aqueous solution contained 260 ppm of the chemical and the atomization operation occurred while rotating the plants on a turntable. Simultaneously, the soil in each pot was drenched with aqueous dispersions of each chemical in the amount of 25 lb/acre. After 7 days, observations are made on the eradication of established infection present on the primary leaves at the time of spraying. The leaves were rated on a scale of from 0 (no suppression) to 10 (complete eradication). The test results are given in Table IV.

RICE LEAF SPOT

The fully expanded young leaves of a rice, cultivar Starr Bonnet, which were about two weeks old and growing in 2½ inch pots, were sprayed with an aqueous solution which contained the test chemical. The young plants were sprayed while rotating on a turntable with the aqueous solution which contained 130 ppm of the chemical. After the spray dried, the plants were atomized with a conidial suspension of Rice brown spot (*Helminthospoium oryzae* B. de H.) and placed in a moist chamber at 75° F. for 24 hours to facilitate infection. After discrete lesions appeared in the unprotected controls (two days later), the infection was rated on a scale of from 0 (no inhibition) to 10 (complete inhibition of infection). The test results are given in Table IV.

POTATO LATE BLIGHT (*PHYTOPHTHORA INFESTANS*)

Test plants were prepared by rooting cuttings from stock plants in perlite. When suitable root systems had initiated, the cuttings were transplanted into pots containing a sandy loam soil. The transplants were held until they had reached the 3-4 leaf stage and were then used for testing. An aqueous suspension of the test compound was applied to the leaves as a spray in the amount of 130 ppm. After application of the test material, the plants were inoculated by spraying them with a suspension of sporangoia washed from agar cultures of *Phytophthora infestans*. The inoculated plants were held at 100% relative humidity and 20° C. for 24 hours, then held in a light room at 20° C. until disease control was assessed. Disease control was rated on a scale of 0 to 10 where 0=no control and 10=100% control. See Table IV for the results of these tests.

TABLE IV

FUNGICIDAL ACTIVITY AGAINST BEAN POWDERY MILDEW, RICE LEAF SPOT AND POTATO LATE BLIGHT

| Test Chemical | Primary Screening | | |
|---|---|---|---|
| | Bean Powdery Mildew | Rice Leaf Spot | Potato Late Blight |
| 5-Benzamido-3-Trichloromethyl-1,2,4-Thiadiazole | 9 | 9 | 7 |
| 5-(2-Toluamido)-3-Trichloromethyl-1,2,4-Thiadiazole | 0 | — | — |
| 5-(3-Toluamido)-3-Trichloromethyl-1,2,4-Thiadiazole | 2 | — | — |
| 5-(4-Toluamido)-3-Trichloromethyl-1,2,4-Thiadiazole | 0 | — | — |
| 5-(4-Anisamido)-3-Trichloromethyl-1,2,4-Thiadiazole | 0 | — | — |
| 5-(3-Nitrobenzamido)-3-Trichloromethyl-1,2,4-Thiadiazole | 2 | — | — |
| 5-(4-Nitrobenzamido)-3-Trichloromethyl-1,2,4-Thiadiazole | 10 | — | — |
| 5-(3,5-Dinitrobenzamido)-3-Trichloromethyl-1,2,4-Thiadiazole | 0 | — | — |
| 5-(2-Chlorobenzamido)-3-Trichloromethyl-1,2,4-Thiadiazole | 1 | — | — |
| 5-(2-Fluorobenzamido)-3-Trichloromethyl-1,2,4-Thiadiazole | 0 | — | — |
| 5-(2,6-Dichlorobenzamido)-3-Trichloromethyl-1,2,4-Thiadiazole | 9 | — | — |
| 5-(2,4-Dichlorobenzamido)-3-Trichloromethyl-1,2,4-Thiadiazole | 0 | — | — |

MEXICAN BEAN BEETLE

Leaves of young bean plants were removed from the plants by cutting the petioles and were dipped into the test chemical at 260 ppm for the primary test. These were placed in a water reservoir to maintain leaf turgidity and, after the chemical deposit was dry, ten 4-day old larvae of the Mexican bean beetle were placed on them. After 5 days, observations were made on the mortality of the immature form and feeding inhibition. Any effects on metamorphosis were noted. Control was rated on a scale of from 0 (no control) to 10 (100% control). See Table V for the results of these tests.

TABLE V

INSECTICIDAL ACTIVITY AGAINST MEXICAN BEAN BEETLE

| Test Chemical | Effect | Primary Screening 260 ppm |
|---|---|---|
| 5-Benzamido-3-Trichloromethyl-1,2,4-Thiadiazole | Mortality | 3 |
| | Feed Inhibition | 6 |
| 5-(2-Toluamido)-3-Trichloromethyl-1,2,4-Thiadiazole | Mortality | 3 |
| | Feed Inhibition | 6 |
| 5-(3-Toluamido)-3-Trichloromethyl-1,2,4-Thiadiazole | Mortality | 8 |
| | Feed Inhibition | 7 |
| 5-(4-Toluamido)-3-Trichloromethyl-1,2,4-Thiadiazole | Mortality | 10 |
| | Feed Inhibition | 9 |
| 5-(4-Anisamido)-3-Trichloromethyl-1,2,4-Thiadiazole | Mortality | 2 |
| | Feed Inhibition | 6 |
| 5-(3-Nitrobenzamido)-3-Trichloromethyl-1,2,4-Thiadiazole | Mortality | 10 |
| | Feed Inhibition | 9 |
| 5-(4-Nitrobenzamido)-3-Trichloromethyl-1,2,4-Thiadiazole | Mortality | 10 |
| | Feed Inhibition | 10 |
| 5-(3,5-Dinitrobenzamido)-3-Trichloromethyl-1,2,4-Thiadiazole | Mortality | 0 |
| | Feed Inhibition | 1 |
| 5-(2-Chlorobenzamido)-3-Trichloromethyl-1,2,4-Thiadiazole | Mortality | 9 |
| | Feed Inhibition | 9 |
| 5-(2-Fluorobenzamido)-3-Trichloromethyl-1,2,4-Thiadiazole | Mortality | 9 |
| | Feed Inhibition | 9 |
| 5-(2,6-Dichlorobenzamido)-3-Trichloromethyl-1,2,4-Thiadiazole | Mortality | 4 |
| | Feed Inhibition | 6 |
| 5-(2,4-Dichlorobenzamido)-3-Trichloromethyl-1,2,4-Thiadiazole | Mortality | 9 |
| | Feed Inhibition | 9 |

What is claimed is:

1. A compound of the formula:

$$Cl_3C-C{=}N \quad \quad O$$
$$\| \quad \quad \| $$
$$N \quad C-NHC-R$$
$$\backslash S /$$

wherein R is phenyl which is unsubstituted or substituted by at least one member selected from the group consisting of lower alkyl having 1 to 4 carbon atoms, lower alkoxy having 1 to 4 carbon atoms, nitro and halo.

2. The compound of claim 1 wherein R is unsubstituted phenyl.

3. The compound of claim 1 wherein R is phenyl substituted by at least one lower alkyl group having 1 to 4 carbon atoms.

4. The compound of claim 1 wherein R is phenyl substituted by at least one lower alkoxy group having 1 to 4 carbon atoms.

5. The compound of claim 1 wherein R is phenyl substituted by at least one nitro group.

6. The compound of claim 1 wherein R is phenyl substituted by at least one halogen atom.

7. The compound of claim 6 wherein said halogen atom is chlorine or fluorine.

* * * * *